(12) United States Patent
Trainer

(10) Patent No.: US 6,177,983 B1
(45) Date of Patent: *Jan. 23, 2001

(54) METHOD AND SYSTEM FOR THE MEASUREMENT OF SPECIFIC CHARACTERISTICS OF SMALL PARTICLES

(75) Inventor: Michael N. Trainer, Telford, PA (US)

(73) Assignee: Microtrac, Inc., Montgomeryville, PA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/156,792

(22) Filed: Sep. 17, 1998

(51) Int. Cl.⁷ ........................................................ G01P 3/36
(52) U.S. Cl. ........................................... 356/28.5; 356/338
(58) Field of Search ..................................... 356/338, 342, 356/341, 436, 441, 432, 433, 434, 28, 28.5; 128/666; 600/453

(56) References Cited

U.S. PATENT DOCUMENTS 4,596,254 * 6/1986 Adrian et al. ......................... 600/479
5,011,279 * 4/1991 Auweter et al. ..................... 356/28.5
5,587,785 * 12/1996 Kato et al. ........................... 356/28.5
5,781,283 * 7/1998 Dammann et al. .................. 356/28.5

* cited by examiner

Primary Examiner—Frank G. Font
Assistant Examiner—Layla G. Lauchman
(74) Attorney, Agent, or Firm—Wood, Herron & Evans, LLP

(57) ABSTRACT

A method for producing measurements of specific key characteristic parameters of small particles suspended within a scattering medium includes the step of directing a beam of light into the scattering medium, then detecting the Doppler-shifted components of light scattered by the movement of the suspended particles and unscattered light from the source and generating a first signal representative of the power spectral density of the Doppler-shifted components and unscattered light. The first signal is next applied to a plurality of bandpass filters to generate a plurality of second signals, the magnitude of which are representative of the power spectral density integrated over the bandpass. The first signal is also applied to a low pass filter that generates a third signal, used in deriving the concentration of the particles in the scattering medium. Each second signal is then normalized by dividing each second signal by the third signal, thereby developing a plurality of individual ratiometric signals whose magnitude is representative of a measurement of a specific key characteristic parameter of the particles in the scattering medium.

10 Claims, 2 Drawing Sheets

METHOD AND SYSTEM FOR THE MEASUREMENT OF SPECIFIC CHARACTERISTICS OF SMALL PARTICLES

BACKGROUND OF THE INVENTION

1. Field of the Invention

The present invention relates generally to the field of measuring the size distribution of particles and more specifically to a method and system for measuring specific parameters of small particle characteristics.

2. Discussion of the Related Art

A number of methods exist for determining the size distribution of particulate material for particles in the approximate size range of 0.1 to 100.0 microns in diameter. One such method known and used effectively for determining the size of small particles is by sensing and measuring their Brownian motion. Brownian motion is caused by random collisions between the particles and thermally excited molecules of the dispersing media. The velocity and direction of the motion is random, however, the velocity distribution of many particles averaged over a period of time will approach a known functional form. Since small particles are known to move faster than larger particles, the particle size can be determined by measuring the size-dependent velocity distribution. For example, fiber optic Doppler anemometers such as those disclosed in U.S. Pat. No. 4,637,716 to Auweter et al, patented Jan. 20, 1987, and U.S. Pat. No. 4,818, 071 to Dyott, patented Apr. 4, 1989, are capable of measuring the size of very small particles down to a diameter of approximately 0.005 microns. However, such fiber optic Doppler anemometers have been useful for measuring particle size accurately only when all particles are of a uniform size.

One method presently known for measuring the particle size and distribution of very small particles of multiple sizes is disclosed by U.S. Pat. No. 5,094,532 to Trainer et al, patented Mar. 10, 1992. This patent discloses a fiber optic Doppler anemometer and method that directs a beam of light into a scattering medium which contains moving particles. The frequency of the scattered light is compared to non-scattered light emitted from the scattering medium and results in the generation of a first signal having a magnitude which is indicative of the difference in frequency between the scattered light and the non-scattered light. A second signal is generated having a magnitude which varies with frequency on a linear scale. The frequency scale of the second signal is then translated into a logarithmic scale and deconvolved to determine the size and distribution of moving particles within the scattering medium. The translation and deconvolving requires translation of analog signals to digital signals and subsequent processing by a central processor and a vector signal processor using fast fourier transfer techniques (FFT). In order to solve for an entire known particle size distribution of over 80 particle diameters the method just described must sample over 80 frequencies. Even though this method provides an accurate measurement of particle size and distribution, it does require a long time period to process all of the sample frequencies and, therefore, is best suited for use in a laboratory with samples that have been extracted from a process and prepared for analysis. Additionally, the central computer and vector processor required in his method add to its complexity and expense.

The measurement of particle size distribution finds use in the process industries in the manufacture of pharmaceuticals, chemicals, abrasives, ceramics, pigments and the like where the particle size affects the quality of the manufactured product. There is an advantage in the ability to measure particle size in-situ and on-line during the manufacturing process in order to more effectively and quickly respond to any changes in the process that may affect the quality of the finished product and to apply these measurements to a process control system that controls the manufacturing process.

BRIEF SUMMARY OF THE INVENTION

In accordance to the present invention, there is provided a method for producing measurements of specific key characteristic parameters of small particles suspended within a scattering medium which includes the step of directing a beam of light into the scattering medium, thereby detecting the Doppler-shifted components of light scattered by the movement of the suspended particles and the unscattered source light and generating a first signal representative of the power spectral density of the Doppler-shifted components and unscattered source light. The first signal is applied to a plurality of bandpass filters. Each bandpass filter generates a second signal, the magnitude of which is representative of the power spectral density integrated over the bandpass for a specific key characteristics parameter. The first signal is further applied to a low pass filter that generates a third signal, the magnitude of which represents a measurement of the concentration of the particles in the scattering medium. Each second signal is normalized by dividing each second signal by the third signal, thereby developing a plurality of individual ratiometric signals whose magnitudes are representative of a measurement of specific key characteristic parameters of the particles in the scattering medium.

It is, therefore, an object of the present invention to provide a method and system for effectively and accurately measuring the spectral power of scattered light in a few specific frequency ranges to provide measurement of selected particle size parameters.

It is also an object of the present invention to provide a method and system that is able to measure particle size parameters on-line, for use by a process control system.

BRIEF DESCRIPTION OF THE SEVERAL VIEWS OF THE DRAWINGS

Other objects, features, and advantages of the present invention will be apparent from the following description of a preferred embodiment thereof, taken in conjunction with the sheets of drawings, in which.

DETAILED DESCRIPTION OF THE INVENTION

It should be understood that the system and method for measuring specific characteristics of small particles of the present invention is applicable to both angular light scattering instruments and devices of the type referred to in U.S. Pat. Nos. 5 3,873,206, 4,134,679 and 5,416,580 and also to dynamic light scattering instruments of the type illustrated in U.S. Pat. Nos. 4,637,716, 4,818,071 and 5,094,526 and to any scattering instruments which detect Brownian motion.

Figure 1:
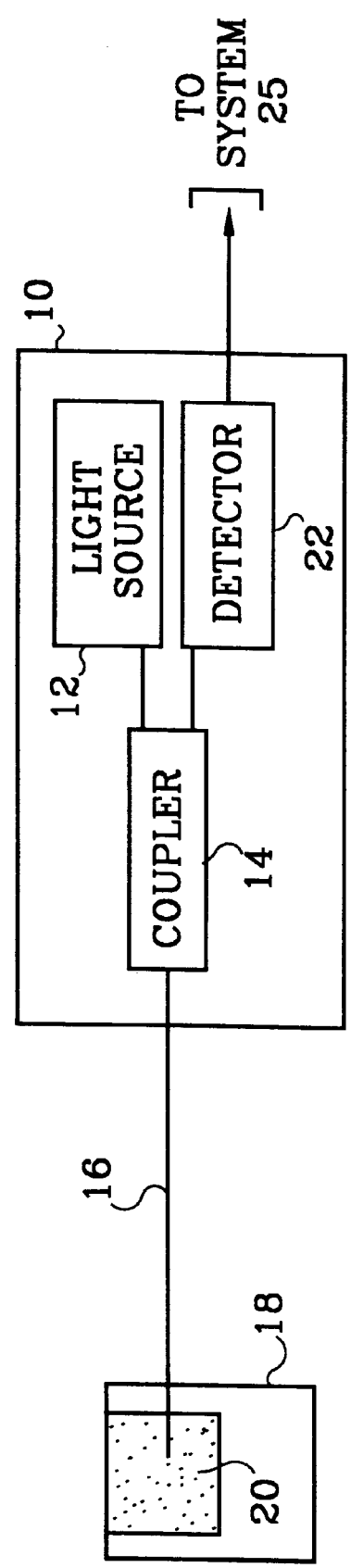
FIG. 1 is a block diagram of a measurement instrument used with the present invention.

Referring to FIG. 1, a dynamic scattering instrument 10 is shown that is used for practicing the method of the present invention. The instrument 10 is preferably an optical Doppler velocimeter and includes a laser diode light source 12, which transmits a beam of light into an optical coupler 14. Light from the coupler 14 is transmitted along an optical cable 16, the end of which is submerged into a sample cell 18 holding the particulate matter 20 suspended in a scattering medium, such as water. The particular scattering medium may be selected from a wide range of media as long as it is inert with respect to the particulate matter suspended therein. Even though optical cable 16 is shown immersed into a sampling cell 18 that is isolated from a manufacturing process, it will be well understood by those skilled in the art that the sampling cell 18 could be part of an apparatus which extracts and prepares representative samples of the manufactured product withdrawn from a conduit transporting the product from one stage of the manufacturing process to another. The prepared sample can be automatically delivered to the sampling cell 18 or delivered to the sampling cell 18 on a demand basis.

The size distribution of the particulate matter 20 is determined by measuring the Brownian motion. Median velocities for typical particles between 0.0005 and 2.0 microns in diameter is on the order of 6000 to 15 microns per second. Such velocities change direction and amplitude continuously, resulting in very small cumulative motion. Light scattering has proven to be the best method to measure such small motions. Light scattered from each particle is Doppler shifted by the particle motion. These Doppler frequency shifts, ranging from a few Hz to several kHz, are proportional to the instantaneous particle velocity. Using frequency beating techniques it is known that one can measure such small frequency shifts which are twelve orders of magnitude smaller than the optical frequency itself.

Light emitted from the immersed end of optical cable 16 is scattered back by the particles 20 into the optical cable 16. In addition, due to the refractive index difference between the glass in the fiber core and the scattering medium, a small portion of the light, emitted from the fiber, is also Fresnel reflected back into the optical cable 16. The Fresnel reflected signal has the optical frequency of the laser diode source 12 and is compared to the frequency of the scattered light from the particles 20. This comparison is made possible since the scattered light is Doppler frequency shifted form the source frequency by the Brownian motion of the particles 20. The scattered and non-scattered (Fresnel reflected) signals are transmitted back through the optical cable 16 and the coupler 14 to photodiode detector 22. In essence the detector mixes the scattered and unscattered light components to produce a stochastic signal indicative of the Doppler spectral broadening of the light scattered by the moving particles. The detector 22 is arranged to sense the fluctuations of light scattered from the particles 20 that are in Brownian motion. The power spectral density of the detector current is high at low frequencies and falls off at higher frequencies. In presently known methods the detector current is filtered, amplified, converted into a digital signal by analog-to-digital conversion means for FFT analysis and power spectrum determination by a local computer or other signal processing device. In order to solve for the entire particle size distribution of the sample (number, volume and area distribution) of 80 particle diameters, the power spectrum must be sampled at 80 frequencies. However, on-line applications that monitor and sense the quality of product production based on particle size distribution usually require less than three characteristics of particle distribution to be measured. For purposes of this embodiment, these characteristics are defined as mean size (mean particle radius), standard deviation and particle concentration. Therefore, only three frequency regions need to be measured to solve for the three identified characteristics.

Figure 2:
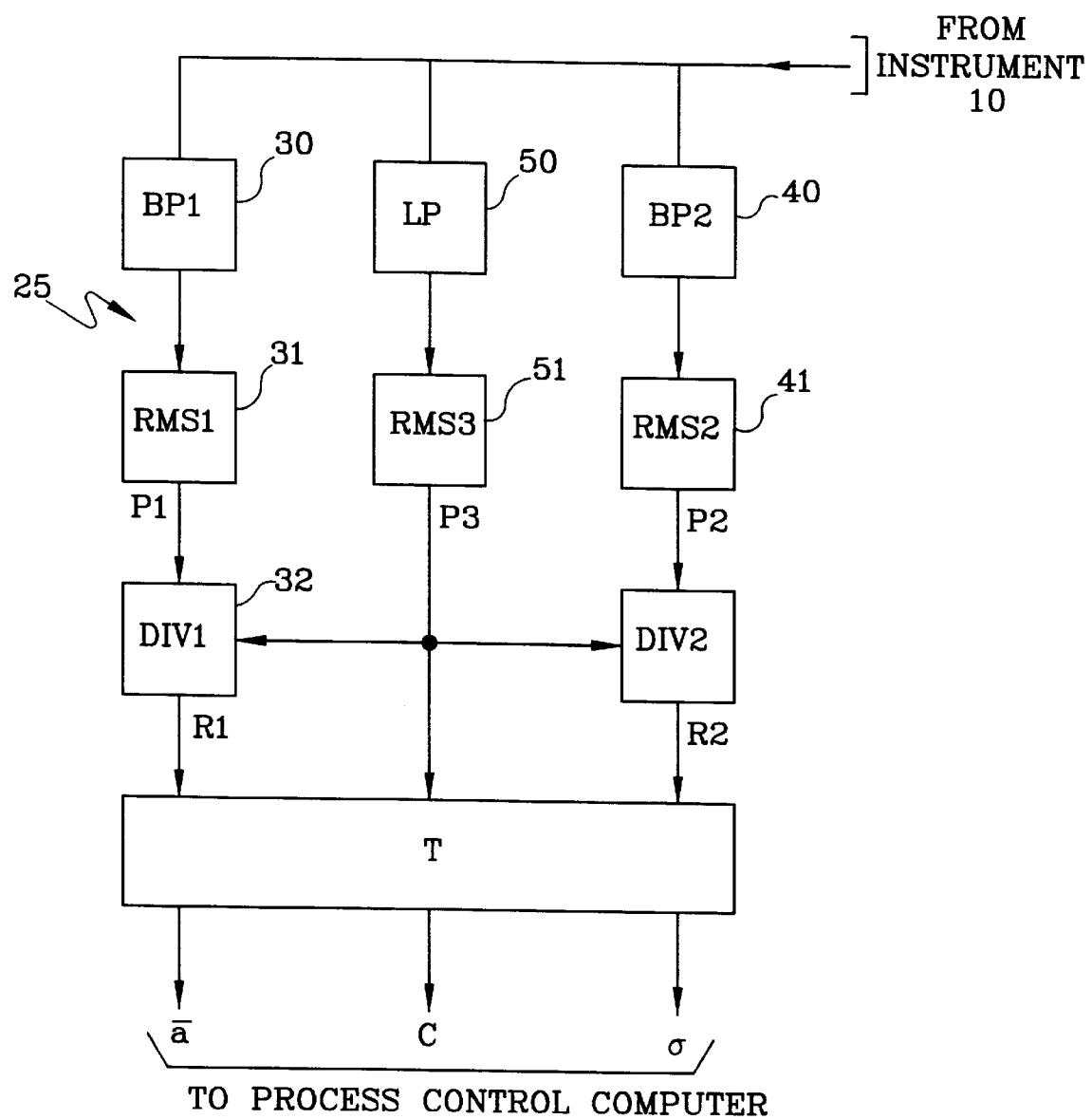
FIG. 2 is a block diagram of a system used to practice the measuring of specific parameters of small particle characteristics in accordance to the present invention.

The present invention accomplishes the measurement of these above-identified characteristics by passing the spectral density of the detector current through three electrical bandpass filters and producing inversion functions of the characteristics being measured. The derived signals so produced can than be directly input into the process control computer of a process control system. FIG. 2, shows a system 25 in accordance to the present invention. The system 25 includes a first bandpass filter 30 (BP1), a second bandpass filter 40 (BP2) and a low pass filter 50 (LP). The photocurrent of the detector 22 is applied to each of the filters 30, 40 and 50 and the outputs of each filter 30, 40 and 50 applied to an associated root mean square circuit RMS1 31, RMS2 41 and RMS3 51, respectively. The outputs of the root mean square circuits 31, 41 and 51 are functions of mean particle radius (P1), standard deviation (P2) and particle concentration (P3), respectively. The two bandpass measurements P1, P2, however, are not independent unless they are normalized by the power of the LP bandpass to account for the particle concentration of the sample. This is accomplished by analog divide circuits 32 (DIV1) and 42 (DIV2). The ratios R1 (P1/P3) and R2 (P2/P3) are provided by the circuits 32 and 42, respectively, and applied to the transformation circuit 60 (T). The circuit 60 receives the normalized ratios R1 and R2 and the analog representation P3 of particle concentration. The normalized values for R1 and R2 are inverted by solving a set of simultaneous equations for the mean particle radius and standard deviation. The output of the transformation circuit is three signals representing the measured particle characteristics $\bar{a}$, $\sigma$ and C, where $\bar{a}$ is the mean particle radius, $\sigma$ is the standard deviation and C is the particle concentration. These three analog power signals can be input into a process control computer for analysis.

In order to better understand the way in which the present invention functions, it may be helpful to understand the mathematical relationships involved in deriving the output signals. As explained earlier, the signal received from the light detector 22 of the dynamic scattering instrument 10 contains the Doppler-shifted components of the stochastic Brownian motion process. The power spectral density of the light detector 22 current can be expressed by the integral equation:

$$S(w) = K \int N(a) \frac{a}{1 + \left(\frac{wa}{B}\right)^2} da$$

where

S(w)=power spectral density

K=instrumental constant w=angular frequency a=particle radius

B=constant which is a function of scattering angle, temperature and viscosity

N(a)=number of particles per unit size interval

To determine the power passed by the analog electronic filters BP1, BP2 of bandpass ($\Delta W$), the power spectral density is integrated over the bandpass and over the total range of particle radii to give the power (P) for each bandpass. This is a function of the particle size distribution and the bandpass.

$$P(\Delta W) = K \int N(a) \int_{\Delta W} \frac{a}{1 + \left(\frac{wa}{B}\right)^2} \, dw \, da$$

The bandpass integral (f) is defined as:

$$f(a, \Delta W) = \int_{\Delta W} \frac{a}{1 + \left(\frac{wa}{B}\right)^2} \, dw$$

When the number of particles per unit size (N(a)) is parameterized, the parameters can be solved for by measuring an equal number of independent bandpass filters. For example, assume that the particle size distribution is Gaussian, with the parameters of mean particle radius, $\bar{a}$, and radius standard deviation σ. Then each bandpass power measurement (P1, P2 of the arrangement above) is a known function of only $\bar{a}$ and σ as shown by equations below:

$$N(a) = \bar{N}(\bar{a}, \sigma, a)$$

$$P(\bar{a}, \sigma, \Delta W) = K \int \bar{N}(\bar{a}, \sigma, a) f(a, \Delta W) \, da$$

where
 $\bar{N}(\bar{a}, \sigma, a)$=Gaussian particle radius distribution (number per unit radius)
 $\bar{a}$=mean particle radius
 σ=standard deviation Using the equations just defined, the mean particle radius is a function of RMS1 and the standard deviation is a function of RMS2.

As can be seen in FIG. 2, the detector current is also applied to the low pass filter 50 and a RMS circuit 51, to output signal P3 representing the particle concentration of the sample. The two bandpass measurements P1 and P2, however, cannot be considered independent unless they are normalized by power P3 from the low bandpass, LP 50, to account for the third unknown, particle concentration. This is accomplished by passing signals P1, P2 and P3 to division circuits DIV1 32 and DIV2 42, where the following normalized values R1 and R2 are derived by the following equations:

$$Pi = P(\bar{a}, \sigma, \Delta W_i)$$

where
 i=1,2,3
then, $$R1 = P_1/P_3$$

$$R2 = P_2/P_3$$

The normalized values R1 and R2 are then inverted by solving the following simultaneous equations for mean particle radius $\bar{a}$, and radius standard deviation a. This is accomplished by the transformation circuit 60 producing the inversion functions $T_a$ and $T_\sigma$.

$$\bar{a} = T_a(R1, R2)$$

$$\sigma = T_\sigma(R1, R2)$$

The method just explained effectively reduces the number of measurements that are made by a particle measurement system and effectively provides for a direct analog transmission of the results to a remotely-located process control computer. This allows for the direct connection of the measured parameters to a remote process control computer, via a standard 4–20 mA current loop, thereby eliminating the need for local analog-to-digital converters, FFT hardware and any local computer or signal processors. Using the method of the present invention a single multi-wire cable would provide power to drive the laser diode and detector of the measurement instrument 10 and return the analog power signals to a process control computer from the analog circuits of the arrangement 25 of the present invention.

In its broadest aspect the present invention teaches a method and system that uses multiple analog signal measurements (in this case spectral bandpass power) to transform analog signal measurements into multiple parameters by a single transformation circuit or network, T. In the present embodiment, the three bandpass power measurements (BP1, BP2, and LP) and the ratiometric signals derived by the DIV1 and DIV2 functions are combined by a single transformation circuit (60) shown in the present invention as being local to the system 25. However, signals P1, P2, and P3 could be transmitted as analog signals to a remotely located process control computer to be transformed into parameters via digital computation, by the process control computer. In such a remote configuration, only a limited number of analog signals can be effectively sent from the measurement instrument to the process control computer over a long distance. The unknown parameters will usually not have a one-to-one correspondence with the analog signals (in this case the power measurements). Each derived parameter of small particle characteristic will usually depend on all of the analog signals and so a set of simultaneous (linear or non-linear) equations would be required to be used to solve for the specific parameters measured. For example LP (50) alone will not provide the particle concentration C without using the signals from BP1 (30) and BP2 (40). However, all three power measurements are proportional to concentration for a fixed particle size distribution.

It will be understood by those skilled in the art that the method just explained is just one of many versions for measuring a particular set of particle characteristics. Any set of other particle parameters can be chosen by the proper definition of N(a), which then would produce the appropriate transformation algorithm T. The number of bandpass filters must be greater than or equal to the number of particle parameters. For example, if the particle size distribution is constant, particle concentration can be measured with one bandpass filter in the high frequency range.

Parameters such as 10%, 50% and 90% of the cumulative volume distribution could be solved with three bandpass filters by assuming a form for N(a). The form for this function is determined from the nominal process being measured so that accurate parameter deviations are generated. This is due because at or near the nominal process control point, the transformation equations of the T circuit 60 will be linear. Since in an automatic process control system, the control parameter only needs to correlate to product quality in order to define a set point, a simple linear T circuit network may be sufficient. In order to improve noise immunity and linearity, the T equations of the T circuits 60 could be replaced with neural networks or other expert systems.

Finally, it will be apparent to those skilled in the art, that the method and system of the present invention can also be effectively applied to apparatus that use only the scattered light components, or a so called "self-beating" measurement system, for determining particle size distribution.

The present invention has been described with particular reference to the preferred embodiments thereof. It will be obvious that various changes and modifications can be made therein without departing from the spirit and scope of the invention as defined in the appended claims.

What is claimed is:

1. A method for producing measurements of specific key characteristic parameters of small particles suspended within a scattering medium, comprising the steps of:

directing a beam of light into the scattering medium;

detecting the Doppler-shifted components of light scattered by the movement of the suspended particles and the unscattered source light and generating a first signal representative of the power spectral density of the Doppler-shifted components and the unscattered source light;

passing said first signal into a plurality of bandpass filters, each bandpass filter generating a second signal, the magnitude of which is representative of the power spectral density integrated over the bandpass for a specific key characteristic parameter;

passing said first signal through a low pass filter to generate a third signal, the magnitude of which represents a measurement of the concentration of the particles in the scattering medium;

normalizing each second signal of said plurality of second signals with said third signal, thereby developing a plurality of individual ratiometric signals whose magnitudes are representative of a measurement of specific key characteristic parameters of the particles in the scattering medium.

2. The method as claimed in claim 1 wherein the method further includes the step of:

transforming said third signal and each of said plurality of ratiometric signals into specific individual inversion functions that represent the magnitudes of specific key characteristic parameters measured.

3. The method as claimed in claim 1 wherein said plurality of bandpass filters includes a first bandpass filter, and said first bandpass filter generates a second signal whose magnitude is a function of at least one of the mean particle radius and the standard deviation of the particle radii of the particles suspended in the scattering medium.

4. The method as claimed in claim 3 wherein said plurality of bandpass filters includes a second bandpass filter, and said second bandpass filter generates a second signal whose magnitude is a function of at least one of the mean particle radii and the standard deviation of the particle radii of the particles suspended in the scattering medium.

5. The method as claimed as claim 4, wherein the step of normalizing divides each of the respective second signals of the first and second bandpass filters by the third signal representing the particle concentration generating said ratiometric signals representative of the mean particle radius of the particles suspended in the scattering medium and of the standard deviation of particle radii suspended in the scattering medium.

6. A system for producing measurements of specific key characteristic parameters of small particles suspended within a scattering medium, used with a measurement instrument that directs light from a light source to a point within said scattering medium comprising:

a detector for detecting the Doppler-shifted components of light scattered by the movement of said suspended particles and light reflected from the scattering medium and generating a first signal representative of the power spectral density of the Doppler-shifted components and reflected light;

a plurality of bandpass filters receiving said first signal and each bandpass filter generating therefrom an individual and specific second signal, the magnitude of which is representative of the power spectral density integrated over the specific frequency of an individual and specific key characteristic parameter;

a filter for receiving said first signal and generating therefrom a third signal, the magnitude of which represents the concentration of the particles in the scattering medium;

a circuit for receiving at least one said second signal and said third signal and developing therefrom a ratiometric signal whose magnitude is representative of a measurement of a specific key characteristic parameter of the particles in the scattering medium.

7. The system as claimed in claim 6, wherein said filter for receiving said first signal is a low pass filter that receives said first signal, generating therefrom said third signal, the magnitude of which represents the concentration of the particles in the scattering medium.

8. The system as claimed in claim 7, wherein said circuit for receiving at least one of said second signal and said third signal is a division circuit associated with an individual one of said plurality of bandpass filters, said division circuit receiving the second signal from its associated bandpass filter and said third signal from said low pass filter and developing therefrom a ratiometric signal whose magnitude is representative of a measurement of a specific key characteristic parameter of the particles in the scattering medium.

9. The method as claimed in claim 1 further comprising:

utilizing said individual ratiometric signals within simultaneous equationsfor mean particle radius and radius standard deviation;

solving said simultaneous equations to yield values for mean particle radius and radius standard deviation.

10. Themethod as claimed in claim 9 further comprising;

utilizing said values for mean particle radius and radius standard deviation and determining a concentration function of particles which is a fuction of mean particle radius and radius standard deviation.

* * * * *

UNITED STATES PATENT AND TRADEMARK OFFICE
CERTIFICATE OF CORRECTION

PATENT NO. : 6,177,983 B1 Page 1 of 1
DATED : January 23, 2001
INVENTOR(S) : Michael N. Trainer It is certified that error appears in the above-identified patent and that said Letters Patent is hereby corrected as shown below:

Column 2,
Line 62, delete "Pat. Nos. 5 5,873,206" and insert -- Pat Nos. 3,873,206 --

Column 4,
Line 33, delete "ā" and insert -- ã --

Column 5,
Lines 17 and 20, delete "ā" and insert -- ã --
Line 59, delete "radius ā, and radius standard deviation a." and insert -- radius ã, and standard deviation σ --

Column 8,
Line 25, delete "at least one said second signal" and insert -- at least one of said second signals --
Line 47, delete "equationsfor" and insert -- equations for --
Line 51, delete "Themethod...;" and insert -- The method...: --
Line 54, delete "fuction" and insert -- function --

Signed and Sealed this

Fifth Day of March, 2002

*Attest:*

JAMES E. ROGAN
*Attesting Officer*     *Director of the United States Patent and Trademark Office*